United States Patent [19]

Stine et al.

[11] Patent Number: 5,157,181

[45] Date of Patent: Oct. 20, 1992

[54] MOVING BED HYDROCARBON CONVERSION PROCESS

[75] Inventors: Laurence O. Stine, Western Springs; Howard E. Fullerton, Arlington Heights; Thomas R. Fritsch, Wheaton; Paul T. Barger, Arlington Heights, all of Ill.

[73] Assignee: UOP, Des Plaines, Ill.

[21] Appl. No.: 621,692

[22] Filed: Dec. 3, 1990

[51] Int. Cl.[5] .............................. C07C 1/00
[52] U.S. Cl. .......................... 585/329; 585/640
[58] Field of Search ..................... 585/329, 640

[56] References Cited

U.S. PATENT DOCUMENTS

| | | | |
|---|---|---|---|
| 2,659,758 | 11/1953 | Detling .................... | 502/38 |
| 3,838,039 | 9/1974 | Vesely et al. ............. | 208/108 |
| 4,499,327 | 2/1985 | Kaiser ..................... | 585/640 |
| 4,859,643 | 8/1989 | Sechrist et al. .......... | 502/37 |
| 4,873,390 | 10/1989 | Lewis et al. ............. | 585/638 |
| 4,879,424 | 11/1989 | Harandi .................. | 585/322 |
| 4,929,780 | 5/1990 | Wright et al. ........... | 585/303 |

FOREIGN PATENT DOCUMENTS

0071437 2/1983 European Pat. Off..
0230792 12/1985 Fed. Rep. of Germany.

*Primary Examiner*—Patrick P. Garvin
*Assistant Examiner*—E. D. Irzinski
*Attorney, Agent, or Firm*—Thomas K. McBride; John G. Tolomei; Richard P. Silverman

[57] ABSTRACT

Moving bed hydrocarbon conversion processes are disclosed wherein a carbonaceous material is deposited on a solid catalyst used in the conversion process to form a coked catalyst which is regenerated in a regeneration zone in order to remove the carbonaceous deposit material from the catalyst and provide a regenerated catalyst having an increased number of active catalyst sites relative to the coked catalyst. The regenerated catalyst is then added to the reaction zone at a rate effective to enhance the conversion to desired products without enhancing the conversion to undesired by-products. When a radial flow reaction zone is employed a relatively constant amount of active catalyst sites can be maintained through the reaction zone by increasing the thickness of annulus through which the catalyst flows in the lower section of the reaction zone wherein the catalyst is more severely coked and has fewer active catalyst sites. The conversion of aliphatic hetero compounds, such as methanol to produce olefins in the $C_2$-$C_4$ carbon range is specifically exemplified.

25 Claims, 1 Drawing Sheet

Figure 1

MOVING BED HYDROCARBON CONVERSION PROCESS

THE FIELD OF THE INVENTION

The present invention relates generally to hydrocarbon conversion processes utilizing a moving bed reaction zone. More particularly the present invention is directed to processes for enhancing the conversion of a hydrocarbon feedstream to a desired hydrocarbon product without enhancing the conversion to by-products such as, for example, in the conversion of methanol to olefins where the olefins are desired products and paraffins are a by-product.

BACKGROUND OF THE INVENTION

Moving bed reaction zones have been proposed for a variety of hydrocarbon conversion processes including: reforming, dehydrogenation, isomerization, hydrocracking, hydrotreating, alkylation, and the like. During such hydrocarbon conversion reactions, a carbonaceous material, i.e., coke, is formed and deposited on a catalyst thereby causing it to deactivate. In the moving bed processes, fresh catalyst particles are fed to a reaction zone, which may be comprised of several subzones, and the particles flow through the zone by gravity. Coked catalyst is withdrawn from the bottom of the reaction zone and transported to a regeneration zone where a regeneration process is employed to remove the carbonaceous material and optionally perform other steps to restore the catalyst activity. Typically, the catalyst also flows through the regeneration zone by gravity and then is withdrawn from the bottom thereof and transported to the top of the reaction zone.

U.S. Pat. No. 3,647,680 issued to Greenwood et al., discloses a method of operating a continuous reforming regeneration process comprising one or more reforming reactors wherein a moving catalyst bed is employed. The patent further discloses that when multiple reactor systems are employed the reactors are preferably stacked vertically with intermediate heating of the reactant stream between the reactors and have a substantially unbroken column of catalyst particles flowing from the top reactor to the bottom reactor.

U.S. Pat. No. 3,838,039 issued to Vesely et al., discloses a method of operating a continuous hydrocarbon conversion process employing a moving bed reaction and regeneration system. The patent discloses that a variety of hydrocarbon conversion processes such as hydrocracking, hydrotreating, hydrofining, reforming, isomerization, alkylation, dehydrogenation, cracking, and shift gas reaction processes can be performed in the moving bed process. The patent discloses that the length of time that the catalyst shall take to completely pass through the reaction zone can be any period depending upon the type of conversion process, the processing conditions, the degree of catalyst deactivation and the quantity of feedstream passed through the reaction zone, e.g., from a period of about a few hours to in excess of a month. See column 11, lines 30-44, The patent does not, however, provide any specific disclosure relating to the catalyst circulation rate and its effect on the conversion to various products or by-products, i.e., selectivity.

U.S. Pat. No. 4,859,643 issued to Sechrist et al., is directed to a method for regenerating coke contaminated catalyst particles which achieves better utilization of oxygen and minimizes surface area loss of catalyst by confining particles in the combustion section of a regeneration zone to a tapered bed configuration. In the method, catalyst particles move through the regeneration zone in continuous or semi-continuous flow and are formed into a vertically elongated bed of particles in the regeneration zone. An oxygen containing gas is passed through the particle bed in a transverse direction and initiates combustion of the coke deposits along a burn front that extends diagonally through the catalyst bed from the inlet surface of the bed to outlet surface of the bed. The catalyst bed is tapered to reduce the volume of catalyst particles behind the burn wave with respect to the gas flow through the bed thereby increasing the gas flow through the upper portion of the bed and removing catalyst that would be exposed to high temperature flue gas flowing across the bed from the burn front.

U.S. Pat. No. 4,879,424 issued to Harandi, discloses a moving bed catalytic process for converting $C_2$-$C_{10}$ aliphatic hydrocarbons to high octane gasoline. The patent discloses that the reaction severity can be controlled by employing sequential reaction zones at different temperatures in order to increase to yield of high quality gasoline.

Typically in hydrocarbon conversion reaction such as described above, by-products are formed in addition to the desired product produced by the hydrocarbon conversion reaction. Often, the by-products are formed when the desired product produced by the hydrocarbon conversion reaction is allowed to remain in contact with active catalyst sites on the catalyst. Additionally, by-products can comprise feedstream reactants or intermediate products that are not converted to the desired product because of insufficient contacting with active catalyst sites on the catalyst, e.g., when the catalyst is coked. As noted from the above-identified patents it is necessary to control the moving bed process in order to obtain the desired products. One commonly used control technique is to employ heating or cooling steps at intermediate points within the moving bed reaction zone or between reaction zones. Another technique is to employ multiple reaction zones having different reactor volumes in order to change the residence time or space velocity to achieve the desired conversion.

One hydrocarbon conversion process where both desired products and by-products are formed is the conversion of methanol to products such as olefins and gasoline where a by-product formed during the reaction comprises paraffins. When producing light olefins, i.e., olefins in the $C_2$ to $C_4$ carbon range, it is not uncommon that paraffins in the $C_1$ to $C_4$ carbon range are also produced.

U.S. Pat. No. 4,499,327 issued to Kaiser, discloses a process for the production of light olefins from a feedstream comprising methanol, ethanol, dimethylether, diethylether, or mixtures thereof, comprising contacting the feedstream with a silicoaluminophosphate molecular sieve at effective process conditions to produce light olefins.

U.S. Pat. No. 4,873,390, issued to Lewis et al., discloses a process for catalytically converting a feedstream, e.g., an aliphatic hetero compound, such as methanol, in to a product, e.g., light olefins, wherein the conversion to olefins can be selectively enhanced as compared to the conversion of to paraffins by employing a catalyst that is not completely regenerated, i.e., contains a desired quantity of carbonaceous material.

U.S. Pat. No. 4,929,780 issued to Wright et al., discloses an integrated process of converting methanol and other lower molecular weights oxygenates to gasoline, distillate range liquid hydrocarbons and ethylene. The patent discloses the use of a fixed bed reactor in conjunction with a fluidized bed reactor in order to increase the yield to ethylene.

In view of the sensitivity of many of the above-described hydrocarbon conversion processes to reaction variables such as temperature, catalytic activity and space velocity, improved processes are sought for controlling the process in order to obtain desired conversion products while inhibiting the conversion to by-products. More specifically, improved moving bed hydrocarbon conversion processes are sought which can provide a sufficient amount of active catalyst sites in order to enhance the conversion to the desired products without enhancing the conversion to by-products.

SUMMARY OF THE INVENTION

By the present invention improved moving bed hydrocarbon conversion processes are provided for the selective conversion of a hydrocarbon feedstream to desired products as compared to by-products. In the moving bed processes of the present invention as the hydrocarbon conversion proceeds a carbonaceous material is deposited on the catalyst moving through the moving bed reaction zone. The amount of carbonaceous deposit material on the catalyst affects the amount of active catalyst sites on the catalyst and thereby influences the extent of the hydrocarbon conversion reaction, and hence the conversion to desired products and by-products. In accordance with the present invention a portion of the coked catalyst is withdrawn from the reaction zone and regenerated in order to remove at least a portion of a carbonaceous material and thereby increase the amount of active catalyst sites. The regenerated catalyst is then added to the reaction zone at a rate effective to enhance the conversion to desired products without enhancing the conversion to by-products. When radial flow reaction zones are employed the catalyst flows through an annulus in the reaction zone and the feedstream passes through the catalyst bed in a transverse direction to the catalyst flow, i.e., across the annulus. In such configurations it is preferred that the thickness of the annulus in the lower section of the reaction zone is greater than the thickness of the annulus in the upper section of the reaction zone in order to provide a relatively constant amount of active sites across the annulus.

In one aspect of the invention there is provided an improvement in a process for converting a hydrocarbon feedstream to a hydrocarbon product stream containing an increased concentration of a product relative to the feedstream comprising contacting the feedstream in a moving reaction zone with a solid catalyst containing active catalyst sites at effective conditions to form the product, a by-product and a coked catalyst containing a carbonaceous material deposited thereon and having a reduced amount of active catalyst sites, withdrawing a portion of the coked catalyst from the reaction zone and regenerating the portion of coked catalyst to remove carbonaceous material and increase the amount of active catalyst sites relative to the coked catalyst and form a regenerated catalyst. The improvement comprises: adding the regenerated catalyst to the reaction zone at a rate effective to provide a sufficient amount of active catalyst sites in the reaction zone to enhance the conversion to the product without enhancing the conversion to the by-product.

In another aspect of the invention there is provided a process for converting aliphatic hetero compounds selected from methanol, ethanol, dimethyl ether, diethyl ether and mixtures thereof to form olefins in the $C_2$-$C_4$ carbon range, comprising; contacting a feedstream comprising at least one of said aliphatic hetero compounds with a solid catalyst containing active catalyst sites in a reaction zone at effective conditions to form the olefins, a by-product comprising paraffins in the $C_1$-$C_4$ carbon range, and a coked catalyst comprising a carbonaceous material and a reduced amount of active catalyst sites, withdrawing a product stream comprising the olefins and the by-product from the reaction zone, withdrawing a portion of the coked catalyst from a lower section of the reaction zone and passing the withdrawn portion to a regeneration zone wherein the coked catalyst is contacted with a regeneration medium at effective conditions to remove at least a portion of the carbonaceous material and increase the amount of active catalyst sites relative to the coked catalyst and form a regenerated catalyst, and adding the regenerated catalyst to an upper section of the reaction zone at a rate effective to provide a sufficient amount of active catalyst sites in the reaction zone to enhance the conversion to the olefins without enhancing the conversion to the by-product.

In still yet another aspect of the present invention there is provided a process for converting aliphatic hetero compounds selected from methanol, ethanol, dimethyl ether, diethyl ether and mixtures thereof to form olefins in the $C_2$-$C_4$ carbon range, comprising; passing a feedstream comprising of at least one of said aliphatic hetero compounds to a lower section of a radial flow, moving bed reaction zone and contacting the feedstream therein with a solid catalyst containing active catalyst sites, said catalyst moving downward through an annulus within the within the reaction zone, at effective conditions to form the olefins, a by-product comprising paraffins in the $C_1$-$C_4$ carbon range, and a coked catalyst comprising a carbonaceous material and having a reduced amount of active catalyst sites, withdrawing a product stream comprising the olefins and the by-product from an upper section of the reaction zone, withdrawing a portion of the coked catalyst from the lower section of the reaction zone and passing the withdrawn portion to a regeneration zone wherein the coked catalyst is contacted with a regeneration medium at effective conditions to remove at least a portion of the carbonaceous material and increase the amount of active catalyst sites relative to the coked catalyst and form a regenerated catalyst, and adding the regenerated catalyst to an upper section of the reaction zone at a rate effective to provide a sufficient amount of active catalyst sites in the reaction zone to provide at least 70% conversion to the olefins and less than 30% conversion to the by-product.

DETAILED DESCRIPTION OF THE INVENTION

The process of the present invention can generally be described as a hydrocarbon conversion process wherein a moving bed of catalyst is maintained within a reaction zone and wherein a carbonaceous material is deposited on the catalyst during the conversion in order to form a coked catalyst. The coked catalyst is then removed from the reaction zone, either continuously or periodically, and regenerated in a regeneration zone in order to remove the carbonaceous material. The regenerated catalyst is then added to the reaction zone.

The processes of the present invention are generally applicable to any type of hydrocarbon conversion process and includes such general processing as hydroprocessing which includes hydrocracking, hydrotreating and hydrorefining; reforming; isomerization; alkylation; dehydrogenation; cracking; and shift gas reaction processes, etc. The conversion process can include all of the above and any other conversion in which a carbonaceous material is laid upon a catalyst rendering it less active than freshly prepared and activated catalyst. In addition to those hydrocarbon conversion processes in which carbonaceous materials are laid upon a catalyst, the present invention is also directed to those processes in which, in addition to the coke laid out, quantities of sulfur, nitrogen or metals are laid upon the catalyst because of their presence in the feedstream. It can then be seen that the term "conversion process" as utilized in the claims can include any type of process in which the catalyst is substantially deactivated by the lay down of carbonaceous materials and, occasionally, other contaminant materials upon the catalyst.

A description of some of the conversion processes suitable for use in accordance with the present invention is set forth in U.S. Pat. No. 3,838,039, hereby incorporated by reference. In general, preferred conversion reactions in accordance with the present invention are those wherein a hydrocarbon feedstream is converted into a hydrocarbon product having an increased concentration of olefins relative to the feedstream. Examples of such preferred hydrocarbon conversions include hydrogenation, reforming, cracking, visbreaking, pyrolysis and dehydration, such as of ethanol to form ethylene. Such processes are often used to produce gasoline range hydrocarbons which are suitable for blending to form a motor fuel. The sources of the feed material described with reference to the above-identified processes and additional uses for the products obtained therefrom are known to those skilled in the art and need not be further disclosed herein.

Substantially any feedstream or combination of feedstreams containing hydrocarbons may be employed in the present invention. The feedstream may be gaseous, solid or liquid at ambient conditions, i.e., 20° C. and atmospheric pressure, but is typically gaseous at the conversion conditions. The feedstream may comprise a combination of inorganic and organic components.

In one aspect, the present invention is used in converting feedstreams having relatively small molecules, i.e., molecules having relatively small kinetic diameters. Aliphatic hetero compounds are particularly preferred feedstreams for use in the present invention, especially when light olefins, i.e., olefins containing 2 to about 6 and preferably 2 to 4 carbon atoms per molecule, and/or gasoline range hydrocarbons are to be produced. The term "aliphatic hetero compounds" is employed herein to include alcohols, halides, mercaptans, sulfides, amines, ethers and carbonyl compounds, e.g., aldehydes, ketones, carboxylic acids and the like. The aliphatic moiety preferably contains from 1 to about 10 carbon atoms, and more preferably from about 1 to 4 carbon atoms. Examples of suitable aliphatic hetero compounds include: methanol; methyl mercaptan; methyl sulfide; methyl amine; dimethyl ether; ethanol; ethyl mercaptan; ethyl chloride; diethyl ether; methylethyl ether; formaldehyde; dimethyl ketone; acetic acid; alkyl amines; alkyl halides and alkyl sulfides. In the aspect of the invention where light olefins and/or gasoline range hydrocarbons are the desired products, the feedstream is preferably selected from methanol, ethanol, dimethyl ether, diethyl ether and mixtures thereof, with methanol being particularly preferred.

The product or products obtained from the conversion process will, of course, depend, for example, on the feedstream, catalyst and conditions employed. Preferably, the desired product is organic. The organic product or products are preferably hydrocarbons in the $C_1$-$C_{12}$ carbon range. In one aspect, the desired product preferably contains olefins having from about 2 to 6, more preferably from about 2 to 4 carbon atoms per molecule. The desired product or products preferably have kinetic diameters which allow such product or products to be removed from or escape from the pores of the catalyst.

Aliphatic hetero compounds such as described above are widely available in the chemical industry. For example, approximately seven billion pounds of methanol were produced in 1989 in the chemical industry, see *Chemical and Engineering News,* Facts and Figures, Page 37, Jun. 18, 1990. In addition, light olefin and gasoline products are widely used within the chemical industry. Light olefins such as ethylene and propylene are known as basic building blocks for the production of chemicals such as: ethylene glycol, ethylene oxide, propylene oxide, methyltertiarybutylether, and various monomers used in the production of polymers such as polyethylene, polypropylene and polyvinylchloride. Gasoline, of course, is used widely as a motor fuel throughout the world.

Reaction conditions for the conversion of aliphatic hetero compounds can be determined by those skilled in the art and, preferably in accordance with the present invention comprise a temperature of from about 200° to 600° C., more preferably from about 300° to 500° C., and a pressure of from about 1 to 200 psia, more preferably from about 20 to 100 psia. Typical of the processes for producing light olefins and/or gasolines are described in U.S. Pat. Nos. 4,499,327, 4,873,390, and 4,929,780 cited above and hereby incorporated by reference. Moreover, a variety of processes have been disclosed for the conversion of light olefins such as ethylene and propylene to gasoline and other hydrocarbons. One such process is disclosed in U.S. Pat. No. 4,942,021 issued to Garwood et al., hereby incorporated by reference.

The particular catalyst used in the conversion process is not a critical aspect of the invention. The selection of a particular catalyst for use in the conversion process depends upon the particular conversion process and other factors known to those skilled in the art which need not be further discussed herein. However, in a preferred aspect of the present invention where an aliphatic hetero compounds are converted into light olefins, it is preferred that the catalysts have relatively small pores. The preferred small pore catalysts are defined as having pores at least a portion, preferably a major portion, of which have an average effective diameter characterized such that the adsorption capacity (as measured by the standard McBain-Bakr gravimetric adsorption method using given adsorbate molecules) shows adsorption of oxygen (average kinetic diameter of about 0.346 nm) and negligible adsorption of isobutane (average kinetic diameter of about 0.5 nm). More preferably the average effective diameter is characterized by adsorption of xenon (average kinetic diameter of about 0.4 nm) and negligible adsorption of isobutane and most preferably by adsorption of n-hexane (average kinetic diameter of about 0.43 nm) and negligible adsorption of isobutane. Negligible adsorption of a given adsorbate is adsorption of less than three percent by weight of the catalyst and adsorption of the adsorbate is over three percent by weight of the adsorbate based on the weight of the catalyst. Certain of the catalysts useful in the present invention have pores with an average effective diameter of less than 5 angstroms. The average effective diameter of the pores of preferred catalysts is determined by measurements described in D. W. Breck, *Zeolite Molecular Sieves* John Wiley & Sons, New York (1974), hereby incorporated by reference in its entirety. The term effective diameter is used to denote that occasionally the pores are irregularly shaped, e.g., elliptical, and thus the pore dimensions are characterized by the molecules that can be adsorbed rather than the actual dimensions. Preferably, the small pore catalysts have a substantially uniform pore structure, e.g., substantially uniformly sized and shaped pore. Suitable catalyst may be chosen from among layered clays, zeolitic molecular sieves and non-zeolitic molecular sieves.

Non-zeolitic molecular sieves include molecular sieves which have the proper effective pore size and are embraced by an empirical chemical composition, on an anhydrous basis, expressed by the formula:

where "Q" is optional and when present, represents at least one element present as a framework oxide unit "$QO_2^n$" with charge "n" where "n" may be $-3$, $-2$, $-1$, $0$, or $+1$; "R" represents at least one organic templating agent present on the intracrystalline pore system; "m" represents the molar amount of "R" present per mole of $(Q_wAl_xP_ySi_z)O_2$ and has a value from zero to about 0.3; and "w", "x", "y" and "z" represent the mole fractions of "Q", aluminum, phosphorus and silicon, respectively, present as framework oxides said mole fractions being within the limiting compositional values or points as follows: w is equal to 0 to 99 mol. %; y is equal to 1 to 99 mol. %; x is equal to 1 to 99 mol. %; and z is equal to 0 to 99 mol. %. "Q" is characterized as an element having a mean "t-o" distance in tetrahedral oxide structures between about 1.51 Å and about 2.06 Å. "Q" has a cation electronegativity between about 125 kcal/g-atom to about 310 kcal/g-atom and "Q" is capable of forming stable Q—O—P, Q—O—Al or Q—O—Q bonds in crystalline three dimensional oxide structures having a "Q—O" bond dissociation energy greater than about 59 kcal/g-atom at 296°]K.

The "Q" of the "QAPSO" molecular sieves of formula (I) may further be defined as representing at least one element capable of forming a framework tetrahedral oxide and may be one of the elements arsenic, beryllium, boron, chromium, cobalt, gallium, germanium, iron, lithium, magnesium, manganese, titanium, vanadium and zinc. Combinations of the elements are contemplated as representing Q, and to the extent such combinations are present in the structure of a QAPSO they may be present in molar fractions of the Q component in the range of 1 to 99 percent thereof. It should be noted that formula (I) contemplates the non-existence of Q and/or Si. When both are non-existent, the operative structure is that of aluminophosphate or $AlPO_4$. When only Q is non-existent, then the operative structure is that of silicoaluminophosphate of SAPO. Thus, the term QAPSO does not perforce represent that the elements Q and S (actually Si) are present. When Q is a multiplicity of elements, then to the extent the elements present are as herein contemplated, the operative structure is that of the ELAPSO's or ELAPO's or MeAPO's or MeAPSO's, as set forth for example by Flanigen et al., in the paper entitled, "Aluminophosphate Molecular Sieves and the Periodic Table," published in the "New Developments and Zeolite Science Technology" Proceedings of the 7th International Zeolite Conference, edited by Y. Murakami, A. Sijima and J. W. Ward, pages 103-112 (1986), said paper hereby incorporated by reference. However, in the contemplation that molecular sieves of the QAPSO variety will be invented in which Q will be another element or elements, then it is the intention to embrace the same as a suitable molecular sieve for the practice of this invention.

Zeolitic molecular sieves in the calcined form may be represented by the general formula;

where Me is a cation, x has a value from about 2 to infinity, n is the cation valence and y has a value of from about 2 to 10.

Typical well-known zeolites which may be used include, chabazite, also referred to as Zeolite D, clinoptilolite, erionite, faujasite, also referred to as Zeolite X and Zeolite Y, ferrierite, mordenite, Zeolite A, and Zeolite P. Other zeolites include those having a high silica content, i.e., those having silica to alumina ratios greater than 10 and typically greater than 100. One such high silica zeolite is silicalite, as the term used herein includes both the silicapolymorph disclosed in U.S. Pat. No. 4,061,724 and also the F-silicate disclosed in U.S. Pat. No. 4,073,865, hereby incorporated by reference. Detailed descriptions of some of the above identified zeolites may be found in D. W. Breck, supra.

The non-zeolitic molecular sieves are preferred in the practice of the present invention for producing light olefins. Among the non-zeolitic molecular sieves, the silicoaluminophosphate molecular sieves (SAPO's) are particularly preferred. SAPO-34, which is described in detail in Example 38 of U.S. Pat. No. 4,440,871, and can be used for promoting the reaction of molecules containing 1 to about 4 carbon atoms, e.g., methane, methanol, methyl halide, and the like, to form products containing up to about 6 preferably up to about 4, carbon atoms per molecule, e.g., ethylene, propylene, butylene and the like.

The preferred catalyst may be, and preferably are, incorporated into solid particles in which the catalyst is present in an amount effective to promote the desired hydrocarbon conversion. In one aspect, the solid particles comprise a catalytically effective amount of the catalyst and at least one matrix material, preferably selected from the group consisting of binder materials, filler materials and mixtures thereof, to provide a desired property or properties, e.g., desired catalyst dilution, mechanical strength and the like, to the solid particles. Such matrix materials are often to some extent porous in nature and may or may not be effective to promote the desired hydrocarbon conversion. The matrix materials may promote conversion of the feedstream and often provide reduced selectivity to the desired product or products relative to the catalyst. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, aluminophosphates, mixtures of these and the like.

If matrix materials, e.g., binder and/or filler materials, are included in the catalyst composition, the nonzeolitic and/or zeolitic molecular sieves preferably comprise about 1% to 99%, more preferably about 5% to about 90% and still more preferably about 10% to about 80%, by weight of the total composition. The preparation of solid particles comprising catalyst and matrix materials is conventional and well known in the art and, therefore, need not be discussed in detail herein.

The operating conditions suitable for use in accordance with present invention depend, of course, on a particular conversion process and can be readily determined by those skilled in the art. Typical reaction parameters which control the reaction severity include temperature, space velocity, catalyst activity and pressure. In general reaction severity increases with increasing temperature, increasing catalyst activity, and decreasing space velocity. The effect of pressure on the reaction severity depends upon the particular reaction. Although in accordance with the present invention any of the above described variables can be adjusted as necessary in order to obtain the desired hydrocarbon conversion, the present invention is particularly directed to the catalyst activity, and more specifically directed to providing an effective amount of active catalyst sites within the moving bed reaction zone in order to enhance the conversion to desired products while not enhancing the conversion to undesired by-products.

Moving bed reaction and regeneration systems suitable for use in accordance with the present invention are those such as described in U.S. Pat. Nos.: 3,652,231; 3,692,496; 3,706,536; 3,785,963; 3,825,116; 3,838,039; 3,839,196; 3,839,197; 3,854,887; 3,856,662; 3,918,930; 3,981,824; 4,094,814; 4,110,081; 4,403,909 and 4,872,969. These patents also describe catalyst regeneration systems and various aspects of moving bed operations and equipment. This reactor system has been widely employed commercially, for example, in, the reforming of naphtha fractions. Its use has also been used for the dehydrogenation of light paraffins, e.g., dehydrocyclodimerization, as well as various other hydrocarbon conversion reactions.

Moving bed reaction zones can be configured in a number of ways, for instance, the catalyst particles can be introduced to an upper section of the reaction zone and fed by gravity through the entire volume of the reaction zone, wherein the catalyst is contacted with the feedstream either in a countercurrent direction to the catalyst movement or in a concurrent direction. In a preferred aspect of the present invention the feedstream flow is countercurrent to the catalyst flow, that it, the feedstream is introduced into a lower portion of the reaction zone and withdrawn from an upper portion thereof. This preferred configuration can provide substantial advantages in many hydrocarbon conversion reactions because the feedstream is thereby contacted with partially deactivated catalyst during the initial stages of the conversion when the driving force is high, and more active catalysts during the subsequent stages of the conversion when the driving force is lower.

More typically the catalyst particles are introduced into an annulus that runs through the reaction zone, wherein the catalyst particles travel down through the annulus and are withdrawn from a lower section of the reaction zone. The feedstream is introduced either to the upper or lower section of the reaction zone and is passed across the annulus generally in a direction transverse to the catalyst flow. The radial bed configuration can provide low pressure drop across the reaction zone, hence well as good flow distribution.

As noted above, during the conversion, a carbonaceous material, i.e., coke, is deposited on the catalyst as it moved downward through the reaction zone. The carbonaceous deposit material has the effect of reducing the number of active sites on the catalyst which thereby effects the extent of the conversion. Thus during the moving bed conversion process a portion of the coked catalyst is withdrawn from the reaction zone and regenerated to remove at least a portion of the carbonaceous material.

Preferably the carbonaceous material is removed from the catalyst by oxidative regeneration wherein the catalyst which is withdrawn from the reactor is contacted with an oxygen-containing gas at sufficient temperature and oxygen concentration to allow the desired amount of the carbonaceous materials to be removed from the catalyst.

Depending upon the particular catalyst and conversion it can be desirable to substantially remove the carbonaceous material, e.g., to less than 1 wt. %, or only partially regenerate the catalyst, e.g., to from about 2 to 30 wt. % carbon. Preferably, the regenerated catalyst will contain about 0 to 20% and more preferably from about 0 to 10% carbon. Additionally, during regeneration there can be oxidation of sulfur and in some instances nitrogen compounds along with the removal of metal materials from the catalyst. Moreover, regeneration conditions can be varied depending upon catalyst used and the type of contaminant material present upon the catalyst prior to its regeneration. It is preferred in most instances when relatively large concentrations of carbonaceous material are present on the catalyst, that is, greater than about 1 wt. percent carbonaceous material on the catalyst, to cause the carbon burn-off to occur with an oxygen-containing gas stream which contains a relatively low concentration of oxygen. Preferably the oxygen content can be regulated through the use of inert gases or the recycling of flue gas materials to maintain an initial oxygen level in the gases which contact the highly carbonaceous containing catalyst of from about 0.5 to about 2 vol percent. By using the small concentration of oxygen, it is possible to reasonably control the oxidation of carbonaceous materials upon the catalyst without allowing excessively high temperatures to occur and preventing the possibility of runaway regeneration conditions within the regeneration zone. The details concerning the conditions for regeneration are known to those skilled in the art and need not be further disclosed herein. The regeneration zone is preferably configured as a moving bed zone similarly to the reaction zone wherein the coked catalyst is fed to an upper portion of the regeneration zone and passed by gravity feed through the regeneration zone wherein the carbonaceous material is removed and the regenerated catalyst is withdrawn from a lower section of the regeneration zone and recirculated to the reaction zone as described above.

The processes of this invention also include, in addition to the hydrocarbon conversion, and carbon burn-off, or regeneration steps, further treatment steps such as, for example, the subsequent sulfiding of the regenerated catalyst to slightly temper its activity when such treatment is required. Such tempering substantially, if not totally, reduces the initial high activity present if the catalyst is not sulfided thereby preventing high rates of degradation in yields. Many processes utilize catalysts which contain metals which must be treated, such as by sulfiding, in order to temper the activity of the catalyst to prevent runaways of low quality yields or high coking rates upon the catalyst. Specifically, such processes which typically require sulfiding are reforming and the hydroprocessing process, although other processes may be utilized which initial catalyst activity is desired to be substantially tempered by a sulfiding step.

In accordance with the present invention the catalyst, after being regenerated to remove carbonaceous deposit material and thereby increase the amount of active catalyst sites, is added to the upper portion of the reaction zone for further contacting with the feedstream. The rate of addition is selected so that a sufficient quantity of active catalyst sites are provided within the reaction zone in order to enhance the conversion of the feedstream to the desired products, without enhancing the conversion to undesired by-products. Thus, if the by-products are formed by the continued conversion of the desired products which are in contact with active catalyst sites, then the rate of the addition of regenerated catalyst is decreased in accordance with the present invention in order to decrease the reaction rates. On the other hand, if the by-products are comprised of feed reactants or intermediate products, then the rate of addition of regenerated catalysts in accordance with the present invention is increased in order to increase the reaction rate and form the desired products. Preferably, the rate of addition is selected to provide at least 70% conversion, more preferably at least 90% conversion to the desired product and less than 30% conversion, more preferably less than 10% conversion to the by-product.

In a preferred aspect of present invention when a radial flow reaction zone is employed, the thickness of the annulus through which the catalyst flows is greater in the lower section of the reaction zone than in the upper section. Thus, the effective residence time in the lower section as the feedstream passes across the annulus in a transverse direction to the catalyst flow will be longer in the lower section of the reaction zone than in the upper section. In this way it is possible to compensate for the higher concentration of carbonaceous material on the coked catalyst in lower section of the reaction zone. Stated another way, since the catalyst in the lower section of the reaction zone will contain a higher concentration of carbonaceous material and therefor a reduced amount of active catalyst sites, the present invention provides a longer residence time in the lower section of the reaction zone in order to compensate for the reduced amount of active catalyst sites. Even more preferably, the thickness of the annulus in the lower section of the reaction zone is effective to provide a relatively constant amount of active sites across the annulus as compared to the upper section. In this aspect of the present invention, the annulus can be tapered in a continuous taper or otherwise the thickness can be increased in one or more step-like changes. Matters concerning pressure drop and flow distribution through the various catalyst thicknesses along the length of the annulus are routine and can be addressed by those skilled in the art.

In another aspect of the present invention the process further comprises the step of sensing a characteristic of the product stream that is indicative of the conversion to the product and by-product and adjusting the rate of withdrawal of the coked catalyst and addition of regenerated catalyst in response to the changes in said conversions. Thus, if the product stream is analyzed and the selectivity to the product is calculated, e.g., by dividing the concentration of the product by the sum of the concentrations of the product and by-product, then the rate of addition of the regenerated catalyst can be increased or decreased as hereinbefore described.

Those skilled in the art will recognize that the reference to a moving bed of catalyst particles contemplates an average turnover of the catalyst in the reaction zone and the regeneration zone. The catalyst may be continuously added and continuously withdrawn from the reactors or the catalyst may be added in intermittent cycles. For instance, every half hour a few hundred pounds of a catalyst may be added to a reactor while at the same time an identical quantity of catalyst is removed from the reaction. It can be seen then that the term "moving bed" does include those instances in which the bed is shifted in a cyclic manner and not necessarily continuously being moved throughout the reaction zone.

Those skilled in the art will further recognize that there exists many aspects of the present invention not specifically disclosed above that are nonetheless within the scope of the claims that follow. For instance located within the reaction zone may be various input streams containing purge or quench streams. Such streams often comprise hydrogen, water, steam or other gaseous or liquid materials which can pass into the reaction zone for purposes of temperature control. Additionally, in many instances it may be desirable to withdraw a portion of the feedstream at intermediate points in the reaction zone and heat or cool the feedstream as required in order to obtain the desired conversion. As noted above, the process of the present invention operates to provide an effective amount of active catalyst sites in order to obtain the desired conversion to the products by controlling the rate of addition of regenerated catalyst to the regeneration zone and optionally in addition by providing an annulus having a varying thickness. Accordingly, by virtue of the present invention it may be no longer necessary, as is many of the prior art processes such as described in above-cited U.S. Pat. No. 4,879,424, to provide sequential reaction zones operating at different reaction parameters such as, for example, different temperatures in order to compensate for the deactivating catalyst, see column 4, lines 21-33, of the patent. However the use of multiple or sequential reaction zones may be desirable and is preferred in certain aspects of the present invention such as, for example, when it is desired to change the residence time or provide substantially different temperatures.

The invention is hereinafter described with reference to the Examples and the Drawing, such description is intended for illustrative purposes and is not intended to limit the scope of the claims that follow.

EXAMPLES

A number of experiments were conducted to demonstrate the effect of catalyst activity on chemical conversion using a small pore molecular sieve catalyst.

The apparatus used in these experiments comprised a ⅛ inch O.D. titanium U-tube reactor which was filled with 36 grams of one-sixteenth inch diameter extrudates, diluted with 36 grams of quartz chips. The extrudates includes about 80% by weight of SAPO-34 and about 20% by weight of silica binder, and were prepared using a conventional catalyst extrusion technique. The reactor temperature was controlled by a fluidized bed heater in which it was located. Pure methanol was fed to the reactor using a 150 rpm FMI metering pump with a model RHOCKC microhead. The methanol was vaporized and preheated in a section of steam jacketed one-inch pipe before entering the reactor. Methanol flow was measured by periodically timing the level change in a burette on the pump suction line. A small rotameter was also used to check methanol flows.

Nitrogen diluent was fed from high-pressure cylinders. It was electrically preheated before mixing with the methanol upstream of the preheater, to help vaporize the methanol. Nitrogen flow was controlled with a Veriflow flow controller, and measured with a 1A-15-1 rotameter.

Pressure in the reactor was controlled with a Grove pressure regulator on the reactor outlet. Pressure was dropped after the reactor outlet to about 5 psig, to avoid condensation in the sample lines. From the reactor, steam-jacketed lines led to the gas chromatograph, then to the two integral orifice blocks used for measuring gas flows. Fittings and other potentially cool areas were electrically heated using heavy duty heat tapes and insulated to prevent any condensation of water or heavy products in the sample lines. The gas stream then went to a condenser and knock-out pot, through a wet test meter, and was vented to a fume hood.

The regeneration was controlled by a set of low wattage ASCO solenoid switching valves, controlled by a Zanadu timer. At the beginning of a regeneration cycle the methanol feed was switched away from the reactor and through a recycle line back to the feed tank; simultaneously, a nitrogen purge was switched on to the reactor. After 20 minutes of purging, regeneration air was switched on, and the catalyst was regenerated for 140 minutes. The reactor was then purged with nitrogen again for 20 minutes before starting the methanol flow again and beginning another run. The regeneration temperature was also controlled via the timer and was gradually increased up to 500° C. during the early part of the regeneration cycle, and the main part of the regeneration cycle the temperature was gradually decreased back down to the starting temperature for the next run. Thus, all regenerations were conducted at 500° C.

The product gas was analyzed with a Varian 3700 gas chromatograph, containing two columns (Carbonsieve S and Porapack R) with thermal conductivity and flame ionization detectors respectively.

The initial sampling time of the GC was controlled by the Xanadu timer, although the time between samples was controlled by a CDS-111 integrator. The column switching which was necessary to obtain the simultaneous TCD and FID analyses was also controlled by the integrator in conjunction with a Varian external events module. Thus, all samples were taken at the same time into the runs.

Samples of the product were taken at times into the run of 10, 40, 70, 100, 130, 160 minutes.

Examples 1 to 12 were conducted at the following reaction conditions:

WHSV, hr$^{-1}$: 1.5
Pressure, psig: 60
$N_2$ Dilution, mole %: 80

The reaction temperature during Examples 1 to 6 was maintained at about 375° C., while the reaction temperature during Examples 7 to 12 was maintained at about 475° C.

Results from these Examples are shown in Table I.

TABLE I

| EX | TIME MIN | $CH_3OH$ Conv % | $DME^1$ | CARBON SELECTIVITY$^2$ | | | | | | |
|---|---|---|---|---|---|---|---|---|---|---|
| | | | | $CH_4$ | $C_2H_4$ | $C_2H_6$ | $C_3H_6$ | $C_3H_8$ | $C_4$ | $C_5$ |
| 1 | 10 | 100.00 | 0.00 | 0.82 | 6.04 | 2.06 | 15.43 | 44.44 | 27.43 | 3.77 |
| 2 | 40 | 100.00 | 0.00 | 0.52 | 15.46 | 1.60 | 43.62 | 10.61 | 26.38 | 1.75 |
| 3 | 70 | 99.70 | 0.26 | 0.47 | 24.16 | 1.37 | 52.06 | 3.60 | 16.62 | 1.71 |
| 4 | 100 | 97.70 | 2.22 | 0.51 | 30.39 | 1.14 | 51.54 | 1.88 | 13.42 | 1.14 |
| 5 | 130 | 82.70 | 17.10 | 0.50 | 31.45 | 0.82 | 50.60 | 1.41 | 14.06 | 1.17 |
| 6 | 160 | 74.40 | 23.12 | 0.88 | 33.58 | 1.03 | 46.83 | 1.77 | 14.43 | 1.47 |
| 7 | 10 | 99.90 | 0.00 | 2.75 | 18.46 | 4.32 | 29.60 | 24.45 | 16.49 | 3.93 |
| 8 | 40 | 100.00 | 0.00 | 3.15 | 34.36 | 2.25 | 41.60 | 3.76 | 12.44 | 2.16 |
| 9 | 70 | 97.50 | 2.38 | 4.01 | 46.65 | 1.22 | 37.01 | 0.92 | 7.85 | 1.31 |
| 10 | 100 | 30.10 | 53.00 | 9.36 | 42.54 | 1.07 | 32.91 | 0.80 | 10.17 | 2.01 |
| 11 | 130 | 13.80 | 67.15 | 13.81 | 31.90 | 1.23 | 27.61 | 0.01 | 12.27 | 1.53 |
| 12 | 160 | 10.40 | 70.21 | 15.27 | 28.14 | 1.61 | 25.32 | 1.21 | 12.86 | 2.01 |

$^1$% of Methanol forming Dimethyl Ether
$^2$% of carbon atoms in the total listed products present in the given product.

As the Examples proceed from 1 to 6 and from 7 to 12, the catalyst is deactivated by the formation of carbonaceous deposit material. The results shown in Table I indicate that propane production, which is a by-product, is reduced as the catalyst becomes deactivated. Maximum ethylene and propylene production is achieved using a particularly deactivated catalyst. Thus, if ethylene and/or propylene are desired products, a window of catalyst activity can be utilized to achieve improved yields of these materials. In order to operate within this window of catalyst activity, in accordance with the present invention, the catalyst is regenerated and recycled to the reactor at an effective rate to provide a sufficient concentration of active sites to enhance the production to ethylene and propylene without enhancing the production to propane a partially deactivated catalyst.

One solution to the selectivity problem is to partially regenerate the catalyst as described and claimed in above cited U.S. Pat. No. 4,873,390. While the present invention does not exclude this solution, in accordance with the present invention the selectivity is controlled by providing the proper amount of active catalyst sites in order to enhance the conversion to light olefins without enhancing the conversion to paraffins. In other words, the effective space velocity of the methanol feedstream, i.e., on the basis of active catalyst sites, is maintained at a relatively constant level. It can be seen from the data that for example, the effective space velocity for Examples 1, 2, and 7 was too high based on the high conversion to propane and the effective space velocity for example 11 and 12 was too low based on the low conversion to ethylene and propylene.

Figure 1:
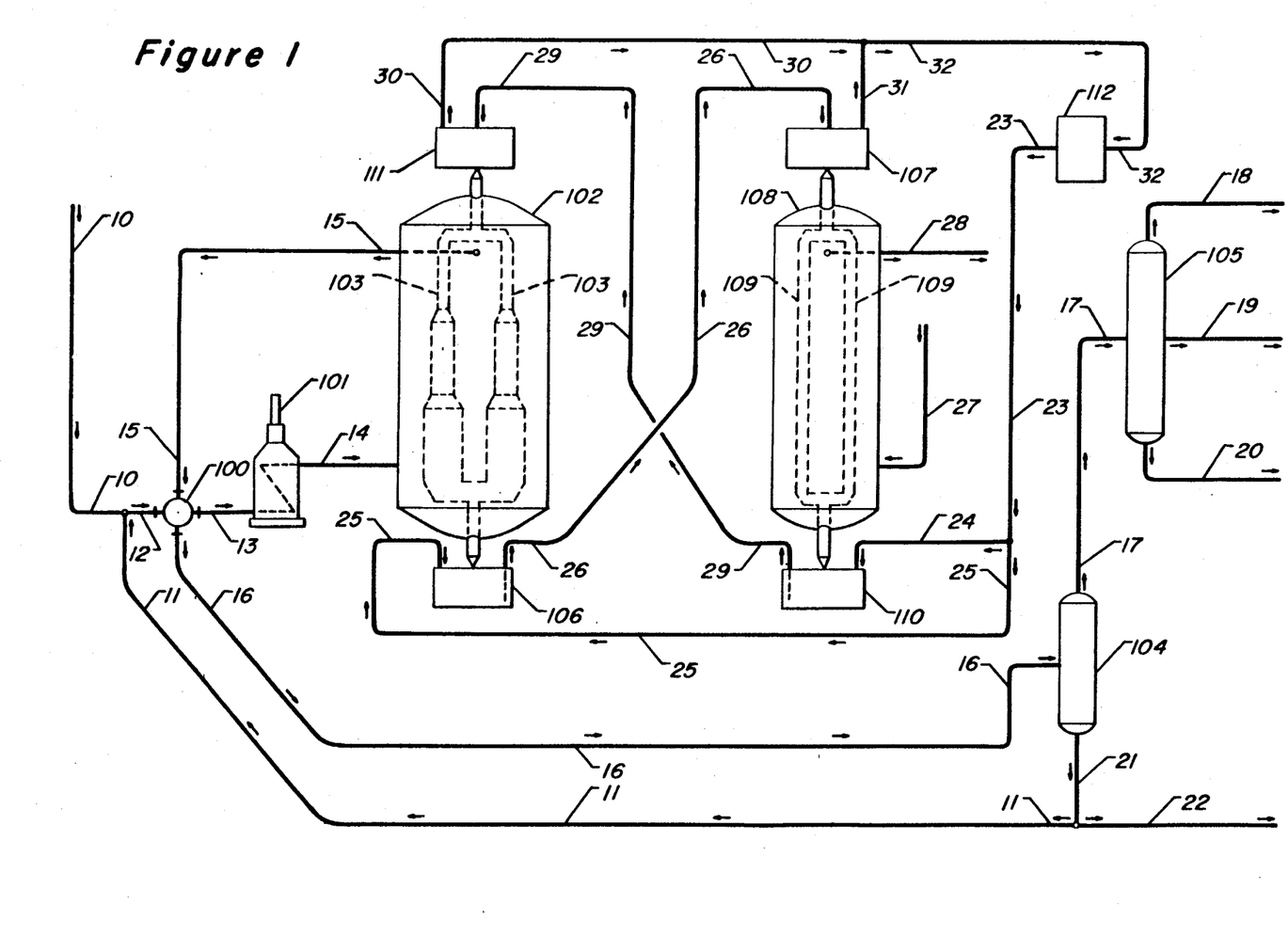
FIG. 1 illustrates a process flow diagram of a process for the conversion of methanol to olefins in accordance with the present invention.

FIG. 1 illustrates a process flow diagram of a process for the conversion of methanol to light olefins in accordance with the present invention. Those skilled in the art will recognize that the process flow diagram has been simplified by the elimination of many necessary pieces of process equipment including some heat exchangers, process control systems, pumps, fractionation column overhead and reboiler systems, etc. It may also be readily discerned that the process flow presented in the drawing may be modified in many aspects without departing from the basic overall concept of the invention. For example, the number of heat exchangers shown in the drawing has been held to a minimum for purposes of simplicity. Those skilled in the art will recognize that the choice of heat exchange methods employed to obtain the necessary heating and cooling at various points within the processes are subject to a large amount of discretion. Accordingly, there exists many possibilities for indirect heat exchange between different process streams. Depending on the specific location and circumstance of the installation of the subject process, it may also be desired to employ heat exchange against steam, hot oil, refrigerant, or process streams from other processing units not shown on the drawing.

Referring to FIG. 1, a methanol feed stream obtained from a methanol plant is passed to the process by line 10 at a pressure of about 20 to 100 psia and combined with stream 11 which comprises water and methanol, the source of which stream is hereinafter defined, to form line 12 which comprises about 25 mol. % methanol and 75 mol. % water. The feedstream in line 12 is then heated by indirect heat exchange in heat exchanger 100 with line 15, the source of which is hereinafter defined and passed by line 13 to heater 101, wherein it is heated to a temperature from about 300°-500° C. The heated feedstream is then passed by line 14 to a lower section of moving bed reaction zone 102 wherein the feedstream is contacted with a moving bed of solid catalyst flowing downward through annulus 103. The schematic of reaction zone 102 and annulus 103 represents a vertical cross-sectional view through the reaction zone. The feedstream passes across the annulus in a direction transverse to the catalyst flow and into the center portion of the reaction zone. It will be noted that the thickness of the annulus is greater at the bottom of the reaction zone than at the top since the catalyst at the bottom of the reaction zone contains a higher carbon content and fewer active catalyst sites. Thus a longer residence time is required at the bottom of the reaction zone in order to maintain the same conversion as at the top of the reaction zone.

The solid catalyst passing through annulus 103 comprises the silicoaluminophosphate molecular sieve known as SAPO-34. The preparation of SAPO-34 is described in detail in above-cited U.S. Pat. No. 4,499,327, hereby incorporated by reference. In the preparation of the catalyst the SAPO-34 is combined with a matrix material comprising about 40 to 60% by weight of alumina binder and formed into spherical particles having a diameter of approximately 1.5 millimeters. Before being used in the process of the present invention, the catalyst is activated, or pretreated by heating in air at a temperature of greater than about 550° C.

A reactor product stream comprising light olefins in the $C_2$-$C_4$ carbon range, as well as paraffin by-products in the $C_1$-$C_4$ carbon range and steam is withdrawn from reaction zone 102 by line 15 and cooled in heat exchanger 100 by indirect heat exchange with the feedstream in line 12 as hereinbefore described. The cooled reactor product stream is withdrawn by line 16 and passed to separation and recovery unit 104 which can comprise a variety of common unit operations well known to those skilled in the art such as flashing units, adsorption and desorption units and distillation units. In separation and recovery unit 104, the hydrocarbon products are separated form the aqueous phase which comprises water and any unreacted methanol. The hydrocarbon product is withdrawn by line 17 and passed to separation and recovery unit 105 wherein the individual hydrocarbon products are separated. Separation and recovery unit 105 also comprise common unit operations known to those skilled in the art such as flashing, refrigeration, compression and distillation. U.S. Pat. No. 4,885,063, issued to Andre, for example, discloses a method for olefin recovery. A methane by-product stream is withdrawn from separation and recovery unit 105 by line 18. A light olefin product stream comprising $C_2$-$C_4$ olefins is withdrawn by line 19. A paraffin by-product stream comprising $C_2$-$C_4$ paraffins is withdrawn by line 20.

A stream consisting essentially of water is withdrawn from the separation and recovery unit 104 by line 21 and a portion thereof is withdrawn from the process by line 22. The remaining portion is passed by line 11 as herein before described and combined with feedstream 10. It should be noted that if stream 21 contains recoverable quantities of methanol it may be desirable to recover the methanol there from by water washing or other means and recycling the methanol to be combined with the feedstream.

As the catalyst flows through reaction zone 102 a carbonaceous material is deposited on the catalyst to form a coked catalyst. The catalyst in the bottom of the reaction zone is passed into catalyst transfer vessel 106 which comprises the appropriate apparatus to engage the catalyst and move it to the regeneration zone, such as, for example, described in U.S. Pat. Nos. 3,838,039 and 4,872,969. The details of the actual operation of the moving bed process including the apparatus for transporting the catalyst is known to those skilled in the art and need not be further disclosed herein. A catalyst transport medium preferably steam, since it is present in the conversion process, is passed by line 23, the source of which is hereinafter defined, and divided into line 24 and 25 and passed to catalyst transfer vessels 110 and 106 respectively. Coked catalyst is withdrawn from catalyst transfer vessel 106 and passed by line 26 to catalyst transfer vessel 107, which contains the appropriate apparatus to disengage the catalyst from the transfer medium, also described in the above-identified patents.

The coked catalyst in transfer vessel 107 is passed through annulus 109 in regeneration vessel 108. In regeneration vessel 108 the coked catalyst is contacted with a regeneration medium, preferably oxygen, in order to remove carbonaceous material and increase the number of active catalyst sites relative to the coked catalyst. The regeneration gas is supplied to regeneration vessel 108 by line 27 at effective conditions to remove the carbonaceous material and the spent regeneration gas is withdrawn from regeneration vessel 108 by line 28. Regenerated catalyst is withdrawn from the bottom of regeneration vessel 108 is passed to catalyst transfer vessel 110 which contains similar apparatus to catalyst transfer vessel 106.

The catalyst transfer medium in line 24, hereinbefore described, is passed through catalyst transfer vessel 110 in order to transport the regenerated catalyst back to reaction zone 102. The regenerated catalyst is passed by line 29 to catalyst transfer vessel 111 which is configured similarly to catalyst transfer vessel 107. Catalyst transfer medium from catalyst transfer vessel 111 is withdrawn by line 30 and combined with catalyst transfer medium in line 31, which is withdrawn from catalyst transfer vessel 107, in order to form line 32 which is then passed to recycle unit 112, wherein the spent catalyst transfer medium can be compressed, pumped, heated, filter or otherwise treated to provide the catalyst transfer medium in line 23 as hereinbefore described.

We claim:

1. A process for converting a feedstream comprising aliphatic hetero compounds to a product comprising light olefins and a by-product comprising paraffin hydrocarbons in a moving bed reaction zone having an upper section and a lower section comprising the following steps:
   (a) contacting the feedstream in said moving bed reaction zone with a solid non-zeolitic catalyst, said moving bed reaction zone containing a concentration of active catalyst sites at conversion conditions to form the product, a by-product and a coked catalyst containing a carbonaceous material deposited thereon to provide a reduced amount of active catalyst sites;
   (b) withdrawing a portion of the coked catalyst from the reaction zone and passing said coked catalyst to a regeneration zone;
   (c) partially regenerating said coked catalyst to remove at least a portion of said carbonaceous material to provide a regenerated catalyst containing active catalyst sites;
   (d) withdrawing the product and the by-product from the moving bed reaction zone and determining a conversion of the feedstream to the by-product and a conversion of the feedstream to the product; and,
   (e) adding a portion of the regenerated catalyst to the moving bed reaction zone at a rate that provides said concentration of active catalyst sites in the moving bed reaction zone to reduce the conversion to the by-product and enhance the conversion to the product.

2. The process of claim 1 wherein the regenerated catalyst is added to an upper section of the reaction zone and is withdrawn from a lower section thereof.

3. The process of claim 2 wherein the feedstream is introduced to an upper section of the reaction zone.

4. The process of claim 2 wherein the feedstream in introduced to a lower section of the reaction zone.

5. The process of claim 4 wherein the moving bed reaction zone is configured to provide radial flow of the feedstream through the catalyst, said catalyst moving downward through an annulus within the moving bed reaction zone.

6. The process of claim 4 wherein the concentration of carbonaceous material on the coked catalyst is greater in the lower section than in the upper section.

7. The process of claim 6 wherein the thickness of the annulus in the lower section of the reaction zone is sized to provide a relatively constant amount of active catalyst sites across the annulus in the upper section and lower section.

8. The process of claim 1 wherein the feedstream comprises aliphatic hetero compounds selected form methanol, ethanol, dimethyl ether, diethyl ether and mixtures thereof.

9. The process of claim 8 wherein the product comprises olefins in the $C_2$–$C_4$ carbon range and the by-product comprises paraffins in the $C_1$–$C_4$ carbon range.

10. The process of claim 9 wherein the rate of addition of regenerated catalyst provides at least 70% conversion to the olefins and less than 30% conversion to the by-product.

11. The process of claim 10 wherein the regenerated catalyst comprises from about 2 to 30 wt. % carbon.

12. The process of claim 1 wherein the solid non-zeolitic catalyst comprises a silicoaluminophosphate molecular sieve.

13. The process of claim 1 wherein the product comprises ethylene and propylene.

14. The process of claim 13 further comprising polymerizing at least a portion of the product to form a polymer.

15. The process of claim 14 wherein the polymer is selected from polyethylene, polypropylene and polyvinylchloride.

16. The process of claim 1 wherein the product comprises gasoline range hydrocarbons.

17. The process of claim 16 further comprising admixing at least a portion of the product with other gasoline blending components to form a motor fuel.

18. A process for converting aliphatic hetero compounds selected from methanol, ethanol, dimethyl ether, diethyl ether and mixtures thereof in a reaction zone having an upper section and a lower section to form olefins in the $C_2$–$C_4$ carbon range, comprising:
   a) countercurrently contacting a feedstream comprising at least one of said aliphatic hetero compounds in the reaction zone with a solid catalyst containing a concentration of active catalyst sites at conversion conditions, depositing a carbonaceous material on active catalyst sites and forming the olefins, a by-product comprising paraffins in the $C_1$–$C_4$ carbon range, and a coked catalyst comprising said carbonaceous material;
   b) withdrawing a product stream comprising the olefins and the by-product from the reaction zone;
   c) withdrawing a portion of the coked catalyst from a lower section of the reaction zone and passing the withdrawn portion to a regeneration zone wherein the coked catalyst is contacted with a regeneration medium at regeneration conditions to remove a portion of the carbonaceous material from the active catalyst sites upon which the carbonaceous material was deposited and increase the amount of active catalyst sites relative to the coked catalyst and form a regenerated catalyst; and
   d) adding the regenerated catalyst to an upper section of the reaction zone at a rate that provides the concentration of active catalyst sites in the reaction zone to enhance the conversion to the olefins without enhancing the conversion to the by-product.

19. The process of claim 18 further comprising sensing a characteristic of the product stream that is indicative of the conversions to the olefins and the by-product and adjusting the rate of addition of the regenerated catalyst in response to changes in said conversions.

20. The process of claim 19 comprising increasing the rate of addition of the regenerated catalyst in response to decreasing conversion to the olefins.

21. The process of claim 19 comprising decreasing the rate of addition of the regenerated catalyst in response to increasing conversion to the by-product.

22. A process for converting aliphatic hetero compounds selected from methanol, ethanol, dimethyl ether, diethyl ether and mixtures thereof to form a product comprising olefins in the $C_2$–$C_4$ carbon range in a radial flow, moving bed reaction zone having an upper section and a lower section, said process comprising;
  a) passing a feedstream comprising at least one of said aliphatic hetero compounds to the lower section of the radial flow, moving bed reaction zone and contacting the feedstream therein with a solid catalyst containing a concentration of active catalyst sites, said catalyst moving downward through an annulus within the reaction zone, at conversion conditions, depositing a carbonaceous material on active catalyst sites and forming the olefins, a by-product comprising paraffins in the $C_1$–$C_4$ carbon range, and a coked catalyst comprising said carbonaceous material;
  b) withdrawing the product and the by-product from the upper section of the radial flow, moving bed reaction zone;
  c) withdrawing a portion of the coked catalyst from the lower section of the radial flow, moving bed reaction zone and passing the withdrawn portion of the coked catalyst to a regeneration zone wherein the coked catalyst is contacted with a regeneration medium at regeneration conditions to remove a portion of the carbonaceous material from active catalyst sites upon which the carbonaceous material was deposited and form a regenerated catalyst having an increased amount of active catalyst sites; and,
  d) adding the regenerated catalyst to an upper section of the radial flow, moving bed reaction zone at a rate that provides the concentration of active catalyst sites in the reaction zone in an amount to provide at least 70% conversion to the olefins and less than 30% conversion to the by-product.

23. The process of claim 22 herein the concentration of carbonaceous material on the catalyst in the lower section of the radial flow, moving bed reaction zone is higher than in the upper section.

24. The process of claim 23 wherein the thickness of the annulus is greater in the lower section of the radial flow, moving bed reaction zone than in the upper section.

25. The process of claim 24 wherein the thickness of the annulus in the lower section of the radial flow, moving bed reaction zone is sized to provide a relatively constant amount of active sites across the annulus in the upper section and lower section.

* * * * *